United States Patent
Gross

(10) Patent No.: US 8,413,272 B2
(45) Date of Patent: Apr. 9, 2013

(54) MEDICAL IMAGING FACILITY AND A MEASUREMENT METHOD FOR DETECTING A POSITION OF A TRANSPORT DEVICE OF THE MEDICAL IMAGING FACILITY

(75) Inventor: Patrick Gross, Langensendelbach (DE)

(73) Assignee: Siemens Aktiengesellschaft, München (DE)

( * ) Notice: Subject to any disclaimer, the term of this patent is extended or adjusted under 35 U.S.C. 154(b) by 189 days.

(21) Appl. No.: 12/968,518

(22) Filed: Dec. 15, 2010

(65) Prior Publication Data

US 2011/0145992 A1    Jun. 23, 2011

(30) Foreign Application Priority Data

Dec. 18, 2009    (DE) .......................... 10 2009 054 916

(51) Int. Cl.
*A47B 13/00*    (2006.01)

(52) U.S. Cl. ............... 5/601; 5/600; 356/4.01; 378/209; 378/205

(58) Field of Classification Search ...... 5/601; 600/410; 378/20, 209, 205
See application file for complete search history.

(56) References Cited

U.S. PATENT DOCUMENTS

| 4,117,337 | A | * | 9/1978 | Staats | 378/17 |
| 5,533,082 | A | * | 7/1996 | Gronemeyer et al. | 378/20 |
| 5,825,843 | A | * | 10/1998 | Kobayashi | 378/20 |
| 6,460,206 | B1 | | 10/2002 | Blasche | |
| 6,721,588 | B2 | * | 4/2004 | Drobnitzky | 600/410 |
| 7,030,615 | B2 | * | 4/2006 | Gortler | 324/318 |
| 7,308,075 | B2 | * | 12/2007 | Barkow et al. | 378/20 |
| 7,831,291 | B2 | * | 11/2010 | Izuhara et al. | 600/415 |

FOREIGN PATENT DOCUMENTS

DE    102008006711 A1    8/2009

* cited by examiner

*Primary Examiner* — Robert G Santos
*Assistant Examiner* — Brittany Wilson

(57) ABSTRACT

A medical imaging facility has a transport device which is able to be moved at least partly in at least one direction. A position detection device has at least one transmit element which detects the position of the transport device and sends out a position measurement beam. The position detection device has at least one detector element and at least one reflector element.

13 Claims, 2 Drawing Sheets

MEDICAL IMAGING FACILITY AND A MEASUREMENT METHOD FOR DETECTING A POSITION OF A TRANSPORT DEVICE OF THE MEDICAL IMAGING FACILITY

CROSS REFERENCE TO RELATED APPLICATIONS

This application claims priority of German application No. 10 2009 054 916.1 filed Dec. 18, 2009, which is incorporated by reference herein in its entirety.

FIELD OF THE INVENTION

The invention relates to a medical imaging facility and a measurement method for detecting a position of a transport device of the medical imaging facility.

BACKGROUND OF THE INVENTION

A medical imaging facility with a transport device able to be moved in at least one direction is already known. The medical imaging facility, for example a magnetic resonance tomography device, a computed tomography device and/or a PET device, is a highly accurate system which demands a precise detection of the position of the transport device to enable a treatment and/or an examination to be undertaken. In this procedure a patient is moved into an imaging area of the medical imaging facility, with the transport device preferably comprising a transport table which is arranged so as to be able to be moved in at least one direction. For determining the position of the movable transport device the medical imaging facility has a position detection device.

In a conventional position detection device a position of the transport device is detected by means of an encoder which is arranged in a drive unit of the transport device and/or is coupled to the latter. This method however involves a high degree of inaccuracy in the detected position of the transport device.

Another known position detection device comprises crosshairs which are moved along with a movement of the transport device. This movement of the crosshairs is detected and the position of the transport device is determined from this. The disadvantage of this method however is that, because of an elasticity and/or expansion of a material of the crosshairs, a high level of inaccuracy is contained in the detected position of the transport device.

Furthermore a position detection device with optical sensors and/or regulators for determining and/or detecting a movement and/or position of the transport device is known. However the disadvantage of this method is that these sensors and/or regulators are arranged at least partly within the imaging area and are therefore subjected to treatment and/or examination radiation. This can adversely affect both the treatment and also the position detection in an undesired manner.

Another known position detection device of a medical imaging facility also features a laser system comprising a laser source for sending out a laser signal and a detector element for receiving the laser signal. The laser signal in this case is beamed directly from the laser source onto the detector element. Usual measurement methods, such as a Time of Flight method, exhibit a high degree of inaccuracy in position determination however. In addition the laser source and/or the detector element are mostly arranged on the movable transport device and is therefore subjected to examination radiation.

SUMMARY OF THE INVENTION

The particular underlying object of the present invention is to provide a medical imaging facility which makes possible precise detection of a position of the transport device. The object is achieved by the features of the claims.

The invention is based on a medical imaging facility with the transport device able to be moved at least partly in at least one direction and a position detection device having at least one transmit element which transmits position measurement radiation for determining a position of the transport device, and at least one detector element.

It is proposed that the position detection device has at least one reflector element. The medical imaging facility is especially formed by a magnetic resonance tomography device, a computed tomography device and/or a PET device and has a imaging area in which an imaging examination of an object under examination, especially a patient, can be undertaken. A reflector element is intended to be understood in this context in particular as an element by means of which incident radiation, especially the position measurement radiation, can be reflected, with the reflection especially occurring explicitly in a pre-determined direction, especially on the detector element or further reflector elements. Preferably the reflector element is arranged along a radiation path of the position measurement radiation between the at least one transmit element and the at least one detector element. The inventive design enables an advantageous multiplicity of a distance from the transmit element to the transport device, especially to a reference point of the transport device as a result of at least one and especially advantageously of a multiple reflection of the position measurement radiation at the at least one reflector element along a path from the transmit element to the detector element. In this manner a precise detection of the position of the transport device can be achieved, in that an inaccuracy in a measurement method can be significantly reduced by the multiplication of the distance.

To detect the position of the transport device the transmit element and/or the detector element can be arranged on the movable transport device. Especially advantageously however the at least one reflector element is arranged on the movable transport device. This enables the transmit element and/or the detector element to be arranged outside the imaging area of the medical imaging facility, so that only the reflector element has to satisfy the stringent demands which are necessary for uninterrupted operation of the medical imaging facility, such as a magnetic resonance-compatible embodiment of the at least one reflector element etc. for example. This enables additional costs for a specific equipping of the transmit element and/or of the detector element to be saved.

It is further proposed that the at least one reflector element be arranged stationary outside the imaging area for recording the movable transport device, by which any hindrance to the movement of the transport device, especially a patient table of the transport device, is able to be prevented. In addition an advantageous multiplicity of a distance in the detection of the position of the transport device can be achieved, especially if the position detection device has at least one first and one second reflector element, with the first reflector element being arranged on the movable transport device and the second reflector element being arranged stationary outside an imaging area for recording the movable transport device. Preferably the second reflector element is arranged stationary on a housing of the medical imaging facility. In addition restricted mounting space within the medical imaging facility can be efficiently used if at least one of the reflector elements is arranged at a small distance from the transmit element and/or the detector element or directly alongside the transmit element and/or the detector element.

Especially advantageously the medical imaging facility has an imaging area for recording the movable transport device, with the at least one transmit element and/or the at least one detector element being arranged stationary outside the imaging area. Low-cost transmit and/or detector elements can advantageously be used which are essentially arranged outside an area through which an examination field or and examination beam passes. In addition the advantage of being able to dispense with additional cables which would have to be moved along with the transport device and which would be required for an arrangement of the transmit element and/or the detector element on the movable transport device can advantageously be dispensed with.

In particular the transmit element and the detector element are arranged on a same opening side of the imaging area on the housing of the medical imaging facility and especially preferably are integrated onto a common circuit board arranged on the housing, so that an advantageous time control for position detection can be achieved between the transmit element and the detector element.

In an advantageous development of the invention it is proposed that a radiation path of the position measurement radiation runs from the transmit element via the first reflector element to at least one further reflector element, which enables an advantageous multiplicity of a distance from the at least one transmit element to the transport device to be achieved. Along with this, for a movement and/or displacement of the transport device by a distance dx, a duplication of the distance dx can also be achieved during a detection of the position of the transport device. A factor of the multiplicity and/or of the duplication is preferably dependent on a number of the reflector elements which are arranged within the radiation path of the position measurement radiation, and/or on a size of individual reflector elements, so that a number of reflections can occur at one reflector element along the radiation path.

In addition an advantageous multiplicity of a distance and/or a displacement can be achieved if a radiation path of the position measurement radiation runs from the at least one further reflector element via the first reflector element to the detector element.

In an advantageous development of the invention it is proposed that at least one reflector element be formed by a retro reflector element. In this context a retro reflector element is especially to be understood as a reflector element in which a reflection of the incident radiation occurs substantially in a direction back to the radiation source of the incident radiation. This embodiment of the invention advantageously enables a space-saving design of the position detection device with a high multiplicity of the distance between the at least one transmit element and the transport device to be achieved. A position detection device designed in this way can be used especially advantageously in the medical imaging device formed by a magnetic resonance tomography device since in this case the space available for mounting the position detection unit is limited.

In addition it is proposed that at least one reflector element is formed by a mirror through which a reflection of the position measurement radiation can be achieved, in which an angle of preferably greater than 0° is enclosed between incident and outgoing, especially reflected radiation. In addition multiple reflections by at least two reflector elements embodied as mirrors can be advantageously achieved by the at least two mirrors being arranged on opposite sides along the radiation path. Especially advantageously the at least one reflector element embodied as a minor has a reflecting surface with a concave curvature so that advantageously undesired beam deviations and/or beam spreading can be compensated for by the concave curvature.

Especially advantageously the at least one transmit element has at least one laser source enabling a universally applicable position measurement beam to be provided which can be employed both in the medical imaging facility embodied as a magnetic resonance tomography device and also in the medical imaging facility embodied as a computed tomography device. The laser source in this case can comprise all types of laser radiation known to the person skilled in the art, such as an infrared laser beam, a microwave laser beam etc. for example.

Furthermore the invention is based on a measurement method for detecting the position of a transport device of a medical imaging facility, whereby in a transmit step a position measurement beam is transmitted by at least one transmit element of the medical imaging facility and in a detection step the position measurement beam is detected by at least one detection element of the medical imaging facility.

It is proposed that the position measurement beam be reflected along a beam path between the transmit step and the detection step at at least one reflector element of the medical imaging facility. Advantageously a multiplicity of a distance between the transmit element and the transport device, especially from a reference point of the transport device, can be achieved as a result of at least one and especially advantageously as a result of a multiple reflection of the position measurement beam at the at least one reflector element along a path from the transmit element to the detector element. In this manner, a precise detection of a position of the transport device can be achieved, in that an imprecision in the measurement method is greatly reduced by the multiplication of the distance. Preferably the medical imaging facility comprises a position detection device featuring the transmit element, the detector element and the at least one reflector element.

It is further proposed that the position measurement beam be reflected at at least one reflector element able to be moved with a transport device. In this case the transmit element and/or the detector element can advantageously be arranged outside the imaging area of the medical imaging facility, so that only the reflector element has to satisfy the strict requirements which are necessary for trouble-free operation of the medical imaging facility, such as a magnetic resonance-compatible embodiment of the reflector element etc.

It is also proposed that the position measurement beam be reflected at at least one further reflector element, whereby advantageously a duplication and/or a multiplicity of a distance and/or of a path distance covered by the transport device can be achieved and in this way an accuracy and/or a precision of the detected position can be increased. Especially advantageously the position measurement beam is reflected for this purpose at at least one further reflector element which is arranged stationary, especially outside the imaging area of the medical imaging facility.

If the position measurement beam is reflected after its transmission by the at least one transmit element, first of all at the first reflector element and subsequently at the at least one further reflector element, an advantageous multiplicity of a distance between the at least one transmit element and the transport device, especially to a reference marking of the transport device, is achieved. As well as this, with a movement and/or displacement of the transport device by a distance dx, a duplication of the change in distance dx can be achieved during a detection of the position of the transport device and thereby an accuracy dependent on a measurement method can advantageously be increased. A factor of the multiplicity and/or of the duplication is preferably dependent on a number of the reflector elements which are arranged within the beam path of the position measurement team and/or on a size of individual reflector elements so that a number of reflections can take place at one reflector element along the beam path. Especially advantageously the position the measurement beam is reflected once again at the first reflector element after a reflection at the at least one further reflector element.

Furthermore it is proposed that a position of a transport device of the medical imaging facility is detected absolutely, whereby advantageously a movement and/or a displacement of the transport device with reference to a reference position such as after each displacement of the transport device for example for detecting a relative displacement can be prevented. In addition a current position of the transport device can be detected directly by this method.

BRIEF DESCRIPTION OF THE DRAWINGS

Further advantages emerge from the description of the drawing given below. The drawing shows exemplary embodiments of the invention. The drawings, the description and the claims contain numerous features in combination. The person skilled in the art will expediently also consider the features individually and combine them into sensible further combinations.

The figures show.

DETAILED DESCRIPTION OF THE INVENTION

Figure 1:
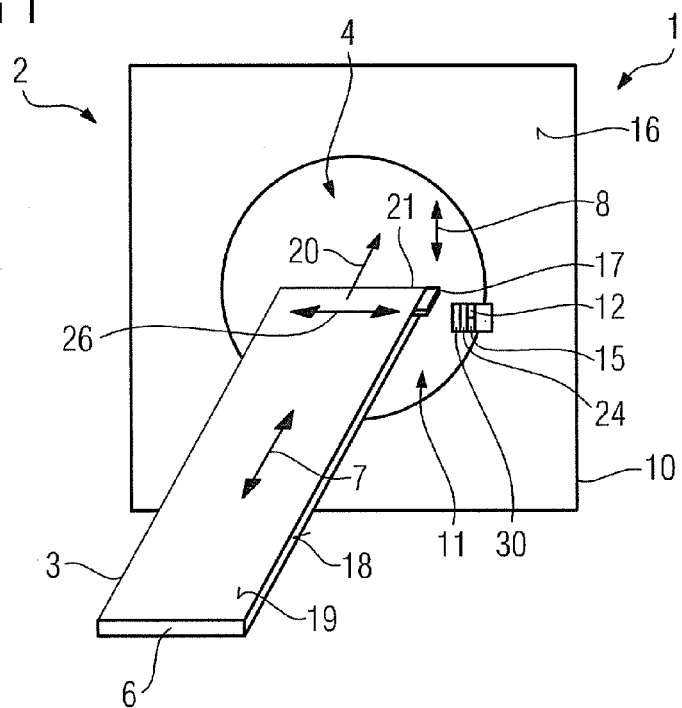
FIG. 1 an inventive medical imaging facility in a schematic diagram.

An inventive medical imaging facility 1, which is formed by a magnetic resonance tomography device 2, is shown in FIG. 1. The magnetic resonance tomography device 2 includes a magnet not shown in any greater detail for generating a strong and constant magnetic field. Furthermore the magnetic resonance tomography device 2 features gradient coils not shown in any greater detail which are provided for generation of a linear gradient field and high-frequency coils not shown in any greater detail. In addition the magnetic resonance tomography device 2 has an imaging area for recording images of an object under examination and/or of a patient for an imaging examination. In an alternate embodiment of the invention the medical imaging facility 1 can also be formed by a computer tomography device and/or a PET device.

The medical imaging facility 1 also includes a transport device 3 which includes a patient table 6 and is disposed to enable it to be moved in a z direction 7. The z direction 7 runs in parallel to the surface normal of an imaging opening of the cylindrical imaging area 4. In addition in a further embodiment of the invention it is always conceivable for the transport device 3 to be arranged to enable it to be moved in other directions, such as for example in a y direction 8 and/or in an x direction 26. The x direction 26, the y direction 8 and the z direction 7 together form an orthogonal system. By means of transport device 3 on which an object under examination and/or a patient is positioned lying down, the object under examination and/or the patient is moved into or out of the imaging area 4 in the z direction 7.

When the medical imaging facility 1 is in operation an examination area is selected for an examination. The examination area comprises a selected slice or a number of selected slices which can be selected by the staff conducting the examination and/or conducting the treatment with the medical imaging facility 1. An image of an examination volume in the patient is to be recorded with the selective layers during operation of the medical imaging facility 1. This requires information about the exact position of the examination volume and/or the patient. The medical imaging facility 1 has a position detection device 11 for this purpose which is designed to detect a position of the transport device 3.

Figure 2:
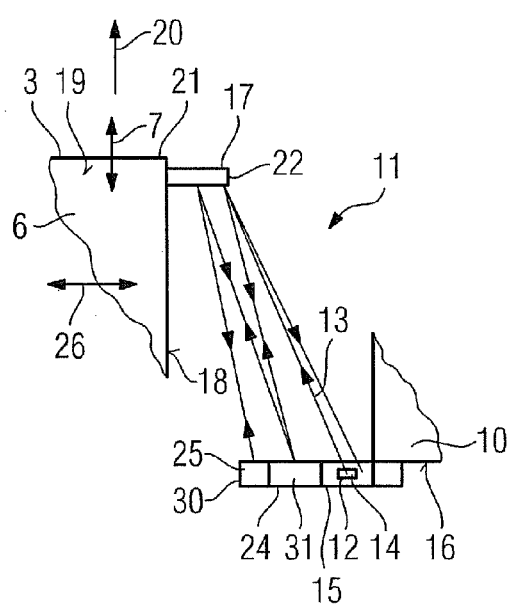
FIG. 2 a schematic detailed view of a position detection device and a transport device of the medical imaging facility and FIG. 3 a flowchart of an inventive method.
Figure 3:
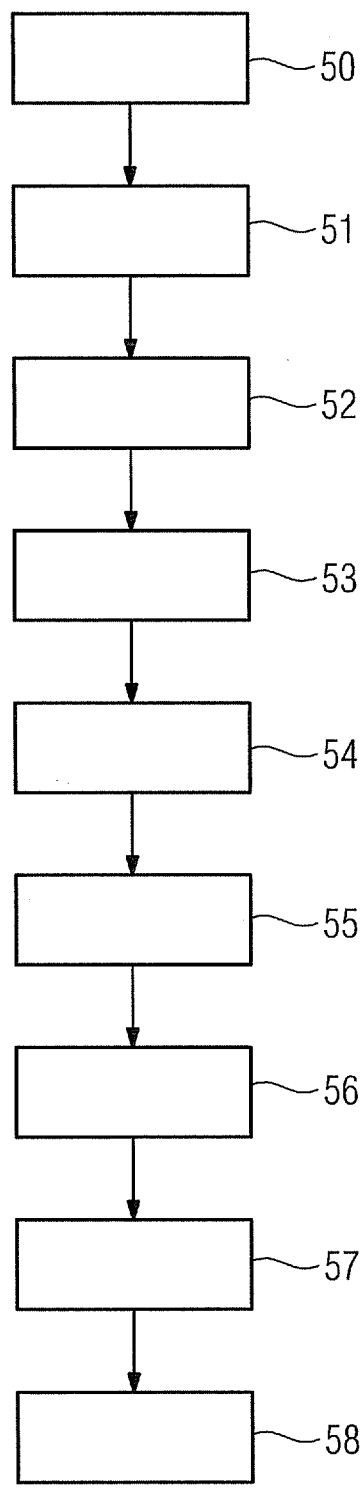

The position detection device 11 is shown in greater detail in FIG. 2 and has a transmit element 12 for transmitting a position measurement beam 13. The transmit element 12 comprises a laser source 14 so that the position measurement beam formed by a laser beam is transmitted during operation of the position detection device. Furthermore the position detection device 11 has a detector element 15 for detection of the position measurement beam 13 transmitted by the transmit element 12. Both the transmit element 12 and also the detector element 15 are arranged stationary outside the imaging area 4 on a housing 10 of the medical imaging facility 1. The transmit element 12 and the detector element 15 are disposed on the same housing side 16 of the medical imaging facility 1 and are integrated onto a circuit board. The transmit element 12 and the detector element 15 can be arranged alongside one another in this case (FIG. 1) or the position detection unit 11 can feature a number of detector elements 15 which are arranged around the transmit element 12 as a central element (FIG. 2). In addition the transmit element 12 and the detector element 15 are arranged along the y direction 8 of the medical imaging facility 1 at a height of the transport device 3, especially the patient table 6 of the transport device 3.

The position of the transport device 3 is detected by means of a conventional measurement method for detecting a distance by means of a position measurement beam 13 formed by a laser beam. This can include a geometric measurement method, for example a triangulation. As an alternative or in addition, the position can also be detected using time detection of the position measurement beam, for example by means of a Time of Flight method. Furthermore a measurement method with a detection of the phase modulation and/or the frequency modulation and/or of a polarization modulation and/or a measurement method formed by interferometry and/or other methods appearing sensible to the person skilled in the art are always conceivable for detecting the position of the transport device 3.

The position detection device 11 also has a first reflector element 17 which is arranged on the transport device 3 able to be moved in the z direction 7, especially on the patient table 6. The first reflector element 17 is arranged on a side surface 18 of the patient table 6 which is essentially aligned at right angles to a support surface 19 of the patient table 6, so that the patient can continue to be comfortably supported during a treatment and/or an examination without any adverse effects. In addition the first reflector element 17 is arranged along a longitudinal extent of the transport device 3, essentially at a front end area 21 along the direction of insertion movement 20 on the transport device 3. The longitudinal extent of the transport device 3 is aligned in parallel to the z direction 8.

The direction of insertion movement 20 reflects a direction of movement of the transport device 3 during a process of inserting the transport device 3 into the imaging area 4. Basically an arrangement of the reflector element 17 on a rear end area and/or on further areas of the transport device 3 which appear sensible to the person skilled in the art are always conceivable.

The first reflector element 17 is formed by a mirror 22, with a mirror surface of the first reflector element 17 being disposed on a side of the first reflector element 17 facing towards the transmit element 12. In addition the mirror surface of the reflector element 17 is embodied concave in order to prevent an undesired beam deviation and/or beam deflection during measurement operation of the position detection device 11.

The position detection device 11 features two further reflector elements 24, 30 (FIGS. 1 and 2). The further reflector elements 24, 30 are arranged together with the transmit elements 12 and the detector element 15 stationary outside the imaging area 4 on the housing 10 of the medical imaging facility 1. In addition the further reflector elements 24, 30 are arranged along the x direction 26 alongside the transmit element 12 and the detector element 15. One of the two reflector elements 24 is likewise formed by a mirror 31 in a similar way to the first reflector element 17 which can likewise have a concave curve and is arranged on the detector element 15 directly next to the latter. The other of the two reflector elements 30 is formed by a retro reflector element 25 which reflects the incident position measurement beam 13 falling on the retro reflector element 25 substantially in a direction of an incident direction. The retro reflector element 25 is arranged directly next to the mirror 30 along the x direction 26. The further reflector elements 24, 30 each have a surface facing towards the first reflector element 17 via which the position measurement beam 17 hits the further reflector elements 24, 30 and subsequently is reflected back in the direction of the first reflector element 17. In an alternative embodiment it is also conceivable for the retro reflector element 25 to be arranged together with the first reflector element embodied as a mirror 22 on the movable transport device 3.

During operation of the position detection device 11 together with the medical imaging facility 1, for detecting the position of the transport device 3, the position measurement beam 13 is initially transmitted by the transmit element 12 in a transmit step 50. The position measurement beam 13 runs substantially in parallel to the longitudinal axis of the transport device 3 and initially strikes the first reflector element 17 formed by the mirror 22. At this location there is a first reflection 51 of the position measurement beam 13 on the first reflector element 17 movable together with the transport device 3. From this first reflector element 17 the position measurement beam 13 is reflected to the further reflector element 24 likewise formed by a mirror 31. At the further reflector element 24 embodied as a mirror 31 there is a second reflection 52 of the position measurement beam 13, with the position measurement beam 13 being reflected back onto the first reflector element 17. At the first reflector element 17 there is a renewed reflection 53 of the position measurement beam 13, with the position measurement beam 13 being reflected onto the retro reflector element 25. During the reflections 51, 52, 53 the incident position measurement beam makes an angle in relation to an outgoing position measurement beam which is greater than zero. At the retro reflector element 25 there is a renewed reflection 54 of the position measurement beam 13, with the reflected position measurement beam 13 being essentially reflected in a direction from which the position measurement beam 13 strikes the retro reflector element 25.

Through the reflection at the retro reflector element 25 the position measurement beam 13 follows a beam path from the transmit element 12 to the retro reflector element 25 in the reverse direction. The position measurement beam 13 is reflected onto the first reflector element 17 from the retro reflector element 25. There the position measurement beam 13 undergoes a reflection 55 in the direction of the further reflector element 30 formed by the mirror 31. From the further reflector element 30 embodied as a mirror 31, there is once again a reflection 56 of the position measurement beam 13 onto the first reflector element 17 and from the first reflector element 17 there is a reflection onto the detector element 15. The position measurement beam 13 striking the detector element 15 is detected and/or recorded in a detection step 58 by the detector element 15. A beam path of the position measurement beam 13 thus runs from the transmit element 11 via the first reflector element 17 to the further reflector element 24 formed by the mirror 31 and from this further reflector element 24 once again via the first reflector element 17 to the retro reflector element 25. From the retro reflector element 25, the beam path of the position measurement beam 13 initially runs via the first reflector element 17 to the further reflector element 24 formed by the mirror 31 and from this once again via the first reflector element 17 to the detector element 15.

The detector element 15 in the detection step 54 detects a characteristic variable of the position measurement beam 13 which depends on the respective measurement method for detecting the position of the transport device 3. The characteristic variable detected is conveyed by the detector element 15 to a processor unit of the position detection device 11 not shown in any greater detail. In the processor unit the characteristic variable measured by the detector element 15 is evaluated and the position of the patient table 6 of the transport device 3 is determined. The position of the patient table 6 is determined in this case in absolute terms by the processor unit so that additional reference measurements for a relative position determination of the patient table 6 can be avoided.

The multiple reflexion 51, 52, 53, 54, 55, 56, 57 of the position measurement beam 13 means that the position measurement beam 13 travels eight times the distance between the transmit element 12 and the first reflector element 17. Because of the measurement method a method-independent inaccuracy is present for each position determination which is independent of the distance and independent of a multiple of the distance, so that the method described above for multiplying the distance between the transmitter elements 12 and the first reflector element 17 leads to a high level of accuracy and/or precision in the detection of the position of the patient table 6 of the transport device 3. In addition, with a displacement and/or movement of the transport device 3 by the distance dx because of the seven-times reflection 51, 52, 53, 54, 55, 56, 57 at the reflector elements 17, 24, 30, a change of an overall path length of the position measurement beam 13 by eight times the distance dx is detected. Since the absolute inaccuracy for the path dx is equal to the absolute inaccuracy for eight times the path dx, the change in the distance is detected by this method with a high accuracy and precision.

The examination volume to be examined can thus be matched as exactly as possible with the examination area in at least part spatial matching in that an exact position change of the transport device 3 is possible as a result of the precise position detection. In particular during mapping of large areas and/or organs by means of the medical imaging facility 1 in which a movement of the patient is necessary for complete mapping, a precise position of the transport device 3 and thus of the patient can be detected for positioning.

Precision of the position detection of the transport device 3 is determined by a number of reflections 51, 52, 53, 54, 55, 56, 57, with an accuracy of the position detection increasing with the number of reflections 51, 52, 53, 54, 55, 56, 57. The number of reflections 51, 52, 53, 54, 55, 56, 57 in this case depends on an embodiment of the reflector elements 17, 24 embodied as minors 22, 31 and on a mounting space available for the reflector elements 17, 24 embodied as mirrors 22, 31 between the transport device 3 and a housing wall of the medical imaging facility 1 for delimiting the imaging area. The more space is available for the reflector elements 17, 24, 30 along the x direction, the larger the reflector elements 17, 24 embodied as mirrors 22, 31 can be made. Along with this, a number of maximum reflections 51, 52, 53, 54, 55, 56, 57 of the position measurement beam along the beam path from the transmitter element 12 to the detector element 15 also increases. Provided one of the reflector elements 17, 24, 30 is formed by a reflector element 25 which reflects the position measurement beam 13 for a position detection in the direction of the position measurement beam 13 striking the retro reflector element 25, despite the restricted space available a maximum number of reflections 51, 52, 53, 54, 55, 56, 57 is also achieved. In addition, because of the arrangement of the further reflector element 24 embodied as minor 31 directly next to the detector element 15 and the transmit element 12, a smaller reflection angle can be used, which advantageously increases a number of possible reflections 51, 52, 53, 54, 55, 56, 57.

As well as the stationary arrangement of the retro reflector element 25 on the housing of the medical imaging facility 1, an arrangement of the retro reflector element 25 on the movable transport device 3 together with the first reflector element 17 is always conceivable.

In addition, in a further embodiment of the invention, the first reflector element 17 arranged on the movable transport device 3 can also be formed by a retro reflector element and in addition further reflector elements can be dispensed with. A beam path of the position measurement beam 13 then runs from the transmit element 12 via the retro reflector element arranged on the movable transport device 3 to the detector element 15. With a displacement and/or movement of the transport device 3 by the distance dx, because of the reflection 51 at the retro reflector element, a change of an overall path length of the position measurement beam 13 by double the distance dx is detected in the detector element 15.

In addition, in a further embodiment of the invention, the reflector element 24 embodied as mirror 31 can be dispensed with and only the retro reflector element 25 arranged stationary next to the detector element 15 and the transmit element 12 outside the imaging area 4. In this case the position measurement beam 13 is reflected three times, first at the first reflector element 17 then at the retro reflector element 25 and again at the first reflector element 17 before the position measurement beam 13 strikes the detector element 15.

In addition further alternate embodiments of the position detection device 11 are conceivable which have a different number of reflections to the exemplary embodiments described above.

The position measurement device 11 and the associated measurement method are controlled by a control unit of the medical imaging facility 1 not shown in any greater detail.

The invention claimed is:

1. A medical imaging device, comprising:
a transport device that is able to be moved at least partly in at least one direction; and
a position detection device comprising:
a transmit element that sends out a position measurement beam,
a detector element that detects the position measurement beam for detecting a position of the transport device, and
at least two reflector elements that reflect the position measurement beam,
wherein a first reflector element of the at least two reflector elements is arranged on the movable transport device, and
wherein a second reflector element of the at least two reflector elements is arranged stationary outside an imaging area for imaging the movable transport device.

2. The medical imaging device as claimed in claim 1, wherein the transmit element and/or the detector element is arranged stationary outside an imaging area for imaging the movable transport device.

3. The medical imaging device as claimed in claim 1, wherein a beam path of the position measurement beam runs from the transmit element via the first reflector element to the second reflector element.

4. The medical imaging device as claimed in claim 1, wherein a beam path of the position measuring beam runs from the second reflector element via the first reflector element to the detector element.

5. The medical imaging device as claimed in claim 1, wherein the reflector element comprises a retro reflector element.

6. The medical imaging device as claimed in claim 1, wherein the reflector element comprises a mirror.

7. The medical imaging device as claimed in claim 1, wherein the transmit element comprises a laser source.

8. A measurement method for detecting a position of a transport device of a medical imaging device, comprising:
sending out a position measurement beam by a transmit element;
reflecting the position measurement beam along a beam path by a reflector element; detecting the position measurement beam for detecting the position of the transport device by a detection element; and
reflecting the position measurement beam by a further reflector element.

9. The measurement method as claimed in claim 8, wherein the position measurement beam is reflected by the reflector element that is able to be moved with the transport device.

10. The measurement method as claimed in claim 8, wherein the position measurement beam is reflected by the reflector element that is arranged stationary outside an imaging area for imaging the transport device.

11. The measurement method as claimed in claim 8, wherein the position measurement beam is first reflected by the reflector element and is subsequently reflected by the further reflector element.

12. The measurement method as claimed in claim 8, wherein the position measurement beam is first reflected by the further reflector element and is subsequently reflected by the reflector element.

13. The measurement method as claimed in claim 8, wherein the position of the transport device is detected in an absolute term so that an additional reference measurement for a relative position determination of the transport device is avoided.

* * * * *